United States Patent [19]

Atherton et al.

[11] 4,204,838

[45] May 27, 1980

[54] METHOD OF ANALYSIS

[75] Inventors: John H. Atherton; Derrick C. Dobson; Ian Hodgkinson, all of Manchester; John R. P. Clarke, Runcorn, all of England

[73] Assignee: Imperial Chemical Industries Limited, Great Britain

[21] Appl. No.: 911,515

[22] Filed: Jun. 1, 1978

[30] Foreign Application Priority Data

Aug. 6, 1977 [GB] United Kingdom ............... 23910/77

[51] Int. Cl.² ..................... G01N 21/22; G01N 31/06; G01N 31/22
[52] U.S. Cl. ................................... 23/230 R; 422/66; 422/69
[58] Field of Search ........... 422/66, 68, 69, 87, 422/91, 56, 57; 23/230 R, 232 R

[56] References Cited

U.S. PATENT DOCUMENTS

| | | | |
|---|---|---|---|
| 3,036,893 | 5/1962 | Natelson | 422/66 X |
| 3,368,872 | 2/1968 | Natelson | 422/66 |
| 3,502,438 | 3/1970 | Natelson | 422/66 |
| 3,552,925 | 1/1971 | Fetter | 422/56 X |
| 3,728,081 | 4/1973 | Bidanset | 422/66 |
| 3,992,158 | 11/1976 | Przybylowicz et al. | 422/57 |

FOREIGN PATENT DOCUMENTS 2316111 11/1973 Fed. Rep. of Germany ............. 422/66

Primary Examiner—Arnold Turk
Attorney, Agent, or Firm—Cushman, Darby & Cushman

[57] ABSTRACT

Method for detecting the presence of a substance contained in a fluid medium, which medium also contains particulate matter therein, comprising the addition of at least a portion of the fluid medium to a leaf material capable of separating by diffusion the fluid medium from the particulate matter and examination, using instrumental detection means, for the presence of the substance contained in the fluid medium in a detection area on the leaf material to which the fluid medium has diffused away from the particulate matter. Apparatus for performing the method where the fluid is a liquid is also described.

8 Claims, 3 Drawing Figures

METHOD OF ANALYSIS

This invention relates to a method of analysis.

According to the present invention we provide a method for detecting the presence of a substance contained in a fluid medium, which medium also contains particulate matter suspended therein, comprising the addition of at least a portion of the fluid medium to a leaf material capable of separating by diffusion the fluid medium from the particulate matter and examination, using instrumental detection means, for the presence of the substance contained in the fluid medium in a detection area on the leaf material to which the fluid medium has diffused away from the particulate matter.

While the method is suitable for the separation of particulate matter from a gas phase containing a specific gas which it is desired to detect and/or estimate the method is particularly suitable for the detection of a substance dissolved in a liquid medium which also contains undissolved solid matter suspended therein and the following description of the method will refer to the particular situation where the fluid is a liquid and the particulate matter is solid and the substance to be detected is dissolved in the liquid medium.

Whilst any substance which is soluble in a liquid medium hereinafter referred to as "the soluble substance" may be detected by the present method using suitable instrumental detection means for examining the detection area, hereinafter referred to as "the detection means", the method is particularly suitable where the soluble substance is detectable by a non-contact technique such as, for example, photometry. The method is also suitable where the soluble substance is not detectable directly by a non-contact technique but can be modified, by reaction with a developer applied to the leaf material before, with or after the liquid medium, so as to form a soluble product which is capable of detection by a non-contact technique such as photometry.

The soluble substance itself may not be the primary species being observed by the method but may be the product of reaction of the primary species contained in the liquid medium with a developer added to the liquid medium before it is applied to the absorbent leaf material.

Where the detection means is capable of producing a response which is related to the quantity of the soluble substance present in the detection area, the method is suitable, after appropriate calibration, for the determination of the concentration of the soluble substance in the liquid medium. The method is thus capable of use in monitoring the progress of certain chemical reactions and especially those wherein an insoluble product is formed from at least one soluble reactant and the presence of the insoluble product inhibits direct, in situ, determination of the state of reaction. By the present method a soluble reactant or a more readily detectable soluble product obtained therefrom, by reaction with added developer, can be readily separated from the insoluble product for estimation of the former.

As an example of such a reaction there may be mentioned the azo coupling reaction between a diazonium compound and a coupling component, either or both of which may be soluble in the reaction medium, to produce an insoluble coloured product e.g. a pigment or disperse dyestuff. The state of reaction may be monitored by assessment of the quantity of the diazonium compound or the coupling component either directly or after reaction with a developer so as to produce a more readily detectable substance. As examples of suitable developer for this purpose there may be mentioned (a) coupling components or diazonium compounds capable of reacting with the diazonium compound or coupling component respectively, which are involved in the azo coupling reaction, in order to produce a soluble dyestuff and (b), where either of the reactants contains a group with the structure $=C-C-OH$, ferric chloride, which is known to react with compounds containing this group to produce a coloured entity.

The leaf material is conveniently an absorbent material such as filter or blotting paper through which a liquid may diffuse but may in suitable circumstances comprise other materials. Depending on the size of the leaf material in relation to the amount of liquid medium applied, the detection area may be on the same side of the material to which the liquid medium is applied, on the opposite side or even, where the leaf material is sufficiently thick, on an edge. Alternative leaf materials are for example ultrafiltration membrane or woven textile materials.

The method is suitable for the detection of a soluble substance in a discrete mass or a flowing stream of the liquid medium. It is preferred, especially with a flowing liquid medium, to continuously sample the liquid medium and apply this to a continuously moving leaf material so as to form a continuous detection area. When this area is examined by suitably calibrated detection means a continuous indication can be obtained of the state of the liquid medium with respect to the soluble substance as it passes the point of extraction. Examples of suitable flowing liquid media are continuous reaction media containing insoluble reactants or products, effluent liquors in drains, and rivers or other watercourses which frequently contain a mixture of dissolved and suspended solids.

Where the species to be detected is not readily detectable by a non-contact technique such as photometry it is convenient to continuously mix the sample stream extracted from the liquid medium with a stream of a suitable developer in order to produce a more readily detectable substance which is soluble in the medium. Alternatively the developer may be incorporated in the leaf material or added thereto after application of the liquid medium.

According to a further feature of the invention we provide an apparatus for detecting the presence of a soluble substance in a liquid medium also containing undissolved solid matter suspended therein comprising, support means for a leaf material capable of separating the liquid medium from the undissolved solid matter by diffusion, means for directing at least a portion of the liquid medium on to a surface of the leaf material and instrumental detection means adapted to examine a detection area on the leaf material to which the liquid medium is capable of diffusion away from the undissolved solid matter and capable of detecting the soluble substance or a product developed therefrom on the surface of the leaf material.

Whilst the apparatus is suitable for intermittent operation it is particularly suitable for continuous operation with either a discrete mass or a flowing stream of the liquid medium.

In a form of the apparatus suitable for continuous operation the support means for the leaf material preferably comprises driving means for causing the leaf material to move at a constant speed. For use with such an apparatus the leaf material conveniently comprises a strip or tape which is driven in a direction parallel to its longitudinal axis. Alternatively the leaf material may be circular and arranged for rotation about its centre point by the driving means.

The means for directing the liquid medium into the leaf material conveniently comprises a pipeline leading from the pipe or vessel containing the liquid medium up to the leaf material. The pipeline carrying the liquid medium to the absorbent leaf material may incorporate a pump if this is desirable and also facilities for mixing the liquid medium with a developer suitable for converting the soluble substance into an instrumentally detectable species. Where the leaf material is moving the liquid medium may be laid down on the material in the form of a stripe along the line of motion to one or both sides of which stripe the liquid medium can diffuse.

Any suitable instrument for detecting the soluble substance in the detection area is suitable but preferred apparatus incorporates a photometer and particularly a calibrated photometer providing a response related to the quantity of the soluble substance in the detection area.

In the form of apparatus adapted for continuous detection the instrumental detection means is sited sufficiently far down stream from the point where the liquid medium is applied to the leaf material to allow the liquid medium to diffuse away from the undissolved solids into the detection area and where necessary to allow the soluble substance to react with a developer to form an instrumentally detectable product.

A preferred form of detection means comprises a photometer adapted to detect, preferably quantitatively, the presence of the soluble substance in the detection area in the presence of any other species in that area contained, for example, in the liquid medium or any developer added to the leaf material or to the liquid medium.

The invention will now be further described by way of example only with reference to the accompanying drawings in which FIG. 1 is an elevation of a preferred apparatus, attached to a pipe carrying a liquid medium.

Figure 1:
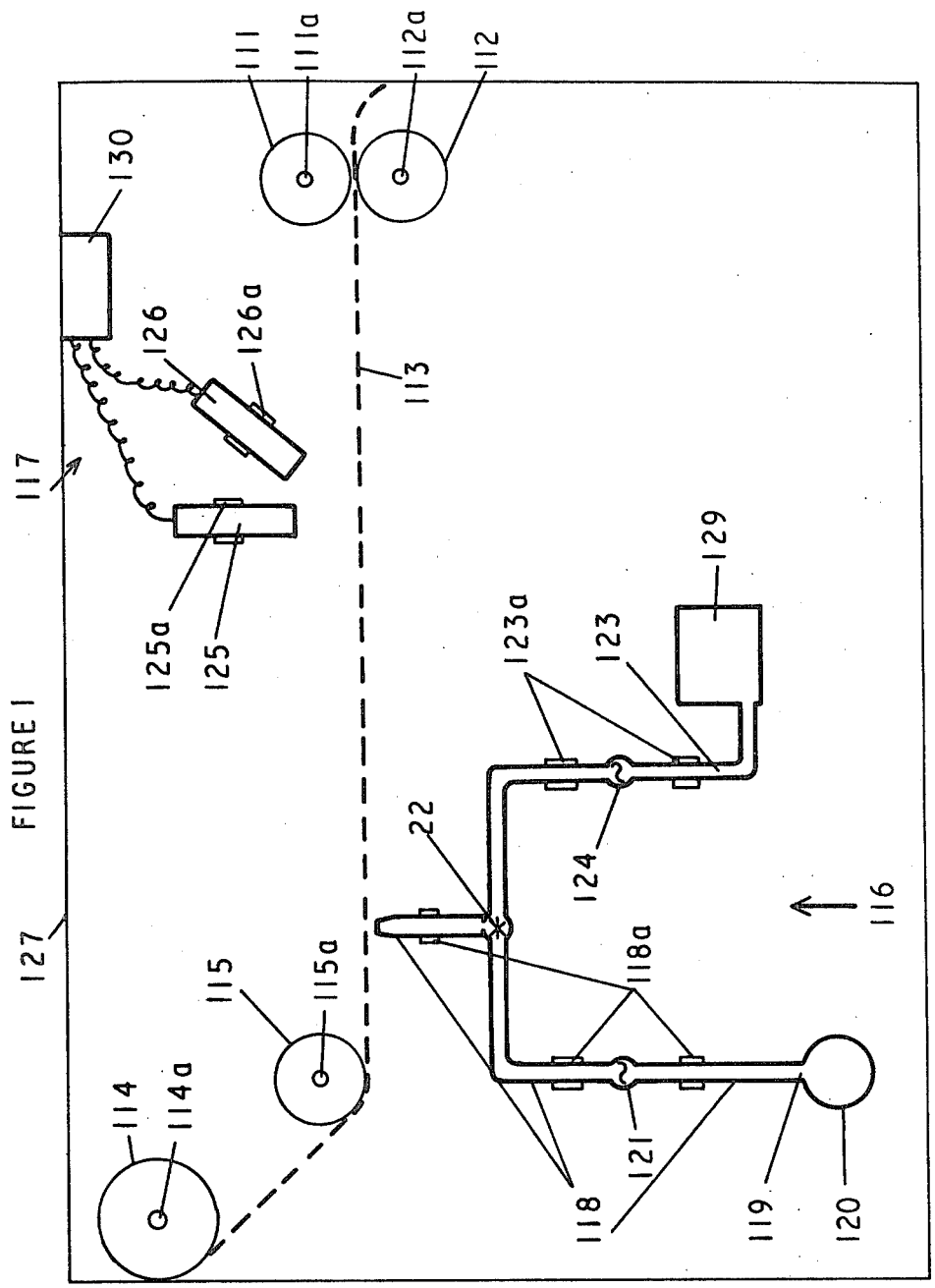
Figure 2:
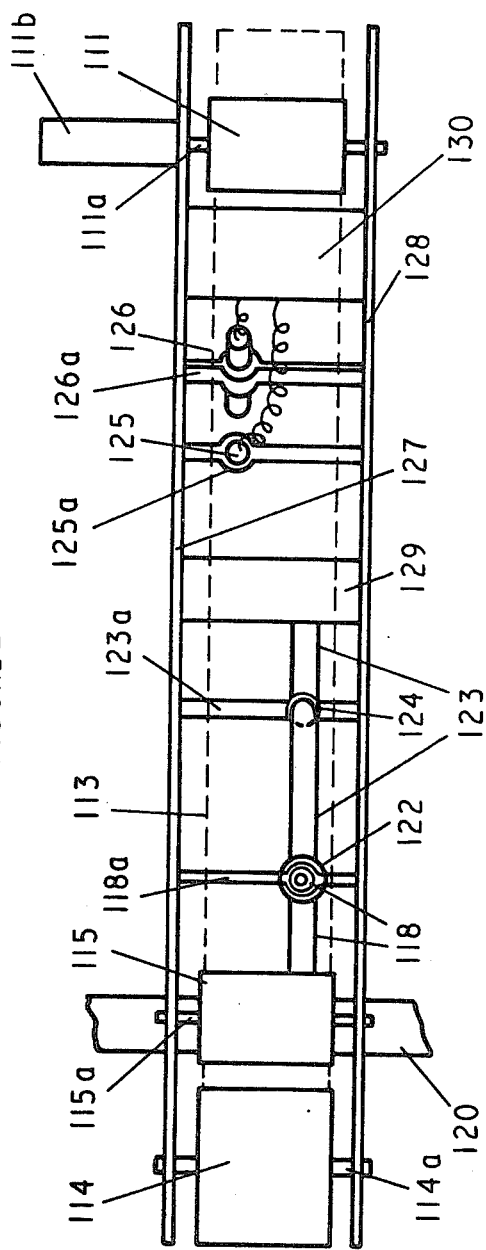
FIG. 2 is a plan view of the apparatus showing in FIG. 1.

In FIGS. 1 and 2, a pair of driven nip rollers 111, 112, mounted on axles 111a, 112a and driven by motors 111b and 112b (not shown) serve to draw an absorbent paper tape 113 from a storage reel 114 mounted on axle 114a round a guide roller 115 mounted on axle 115a and horizontally past a liquid medium application system 116 and photometric detection means 117. The axles 111a, 112a, 114a and 115a are rotatably mounted between frame members 127, 128.

The liquid medium application system 116 comprises a pipeline 118 leading from an extraction point 119 in a pipe 120 carrying the liquid medium via a pump 121 and mixer 122 to within a short distance of the underside of the paper tape 113. A subsidiary pipe line 123 leads from a store of developer 129 via a pump 124 into the mixer 122.

The detection means 117 comprises the light source 125, detector 126 and analyser 130 of a non-specular reflectance photometer. Pipe lines 118, 123, light source 125 and detector 126 are carried by cross-members 118a, 123a, 125a and 126a from frame members 127, 128 which are mounted on pipe 120.

In operation the paper tape is fed from storage reel 114, around guide roller 115 and between the driven nip rollers 111, 112. A portion of the liquid medium flowing through pipe 120 is drawn up pipeline 118 through pump 121 and into mixer 122 where it is mixed with a developer—the developer being drawn through the subsidiary pipeline 123 the developer pump 124 from the developer store 129. The mixture of liquid medium and developer passes on up pipeline 118 from the end of which it is ejected onto the underside of the paper tape at an application position A (see also FIG. 3) towards one lateral edge of the tape 113. The liquid medium spreads out initially on the surface of the paper tape 113 carrying with it the undissolved solid matter but after a short distance the liquid medium is totally absorbed leaving the undissolved solid matter in a band, B, lying towards one lateral edge of the underside of the paper tape 113. The liquid medium continues to diffuse through the paper carrying with it all dissolved material until it reaches the edges of the paper tape at C and $C^1$, so producing broad and narrow bands of liquid medium, D, $D^1$, on either side of the band, B, of undissolved solid matter.

The speed of the paper tape 113, determined by the nip roller 111, 112 is adjusted so that the bands D, $D^1$ are formed before the tape 113 passes under the detecting means 117. The light source 125 and detector 126 of the spectrophotometer are directed at a detection area E which lies on a subsidiary band F in the middle of band D and on the upper side of the paper tape 113.

Figure 3:
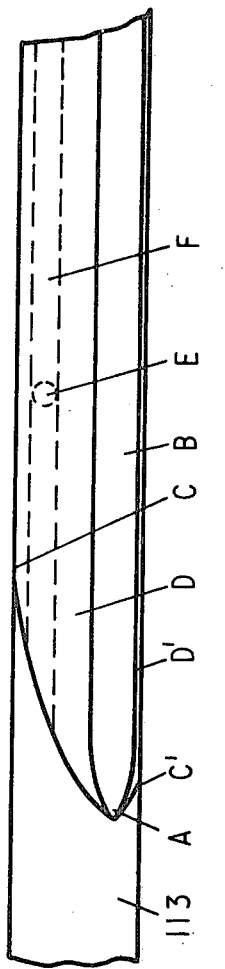
FIG. 3 is a plan view of a paper tape as it passes through the apparatus shown in FIGS. 1 and 2, during operation.

Although the position of application A as shown in FIG. 3 is on the opposite side of the paper tape 113 from the detection area E this is not essential. It is preferred however to apply the liquid medium to the underside of the paper tape to reduce the possibility of undissolved solid matter flooding over onto the liquid band D and affecting the analysis by the detecting means 117.

As an alternative to mixing the developer with the liquid medium in the mixer 122, the developer can be previously impregnated in the tape or added to the tape by means of a second application system up stream or down stream from the position of application A for the liquid medium provided sufficient time is allowed for reaction of the developer with the soluble species before the paper tape 113 passes the detecting means 117.

Where the soluble species is itself directly detectable by the detecting means 117 it is not necessary to provide the mixer 122 and the developer feed system, the liquid medium being added directly to the paper tape 113 at A.

The invention is further illustrated by the following Example which describes how the method may be used to monitor the progress of coupling in the manufacture of azo dyes. The reader will appreciate that the method can also be used in other similar circumstances to monitor the presence of critical species in chemical reaction and other liquid systems particularly where these are flowing.

In the Example all parts and percentages are by weight unless otherwise indicated.

EXAMPLE

Three aqueous dyestuff slurries (A, B and C) are prepared by coupling diazotised 2-bromo-4,6-dinitroaniline on to 5-acetylamino-N-($\beta$-methoxyethoxycarbonylethyl)-2-methoxy-aniline, coupling component, each slurry containing 3% weight/weight of dyestuff, 5% weight/weight of sodium sulphate and 3% weight/weight, as sodium acetate, of a sodium acetate/acetic acid mixture to buffer the pH at 4.5. The slurries contain different excess quantities of the coupling component (A contains 5% excess, B contains 1% excess and C contains no excess) over that required to balance the quantity of diazotised 2-bromo-4,6-dinitroaniline.

In separate runs each slurry is mixed continuously at a rate of 10 mls per minute with 0.1 M solution of diazotised aniline-2,5-disulphonic acid in dilute HCl, developer, flowing at 2 mls per min. in the apparatus shown in FIGS. 1 to 3 of the accompanying drawings.

The developer reacts with the excess coupling component in the slurry to produce a water-soluble dyestuff with an absorption peak at 485 nanometers and an extinction coefficient of $3 \times 10^4$.

The slurry is extracted from pipe 120, fed along line 118 by pump 121 and mixed with developer, flowing along line 123, at mixer 122. The mixture then proceeds along line 118 where it is directed on to the underside of an absorbent paper tape 113 being drawn through the apparatus at 1 mm/sec. by nip rollers 111, 112. The liquor spreads out on the tape and diffuses through to the upper side as shown in FIG. 3 and is examined as it passes under the detection means 117.

The upper surface of the tape 113 is illuminated by a light beam, from the light source, 125, at two wavelengths 485±20 nanometers and 730±20 nanometers, selected by suitable filter in the light path, and a portion of the diffuse reflected light at each wavelength is picked up by the detector 126 which feeds a signal to the analyser 130. The analyser compares the intensities of the reflected light at the two wavelengths and produces an output representative of the logarithm of the ratio of the intensities at the two wavelengths. In each run the analyser output registers a steady output when steady flow conditions have been established.

The results for the three runs using slurries A, B and C are given in the following table:

| Run | Slurry | % mole excess cpupling component | Analyser output |
|---|---|---|---|
| 1 | A | 5 | 1.25 |
| 2 | B | 1 | 1.00 |
| 3 | C | 0 | 0.45 |

From the results a graph is plotted of analyser output against excess coupling component. This graph forms a calibration of the apparatus for its use in monitoring the extent of coupling in the preparation of the said dyestuff using the said developer.

We claim:

1. A method for the detection of a soluble substance dissolved in a liquid which also contains particular matters suspended therein, comprising the steps of:
    adding at least a portion of the liquid to one side of a single continuously moving homogeneous strip of a porous leaf material capable of separating by diffusion the liquid from the particulate matter; and
    examining the surface of the tape downstream from the area at which the liquid was applied and in a detection area on the strip into which the liquid has diffused away from the particulate matter, said examining being accomplished utilizing a non-contact detector.

2. A method as recited in claim 1 comprising the further step of, prior to adding the liquid to one side of the continuously moving strip, treating the liquid with a developer capable of reacting with the soluble substance to produce a soluble photometrically-detectable species; and wherein said examining is accomplished photometrically.

3. A method as recited in claim 1 wherein the detection area is on the opposite side of the strip from the side to which the liquid is applied.

4. A method as recited in claim 1 comprising the further step of producing a response while examining the strip, which response is related to the quantity of the soluble substance in the detection area.

5. A method as recited in claim 1 wherein the liquid is a reaction medium in the production of an insoluble azo pigment or azo dyestuff from at least one soluble reactant.

6. A method as recited in claim 1 wherein said strip consists of a mono-layer of porous paper or textile material.

7. Apparatus for detecting the presence of a soluble substance dissolved in a liquid which also contains undissolved solid matters suspended therein, comprising
    means for supporting and moving in a continuous manner past a liquid application station, and then past an examination station, a single homogeneous strip of porous leaf material so that no separation of the strip into components is practiced;
    means for continuously directing a liquid containing insoluble matter suspended therein onto one side of the strip as it passes the liquid application station; and
    non-contact instrumental detection means for examining a detection area on the strip into which the liquid has diffused away from the undissolved solid matter, and for detecting the soluble substance on the surface of the strip as it passes the examination station.

8. Apparatus as recited in claim 7 wherein said detection means comprises a calibrated photometer.

* * * * *